United States Patent [19]

Hoffman et al.

[11] Patent Number: 4,668,699
[45] Date of Patent: May 26, 1987

[54] NOVEL HMG-COA REDUCTASE INHIBITORS

[75] Inventors: William F. Hoffman; Robert L. Smith, both of Lansdale; Edward Scolnick, Wynnewood, all of Pa.

[73] Assignee: Merck & Co., Inc., Rahway, N.J.

[21] Appl. No.: 762,736

[22] Filed: Aug. 5, 1985

[51] Int. Cl.$^4$ .................. C07D 309/30; A61K 31/365
[52] U.S. Cl. .................................. 514/460; 549/292; 562/501; 560/119; 560/256; 514/824
[58] Field of Search .......................... 549/292; 514/460

[56] References Cited

U.S. PATENT DOCUMENTS

| 4,346,227 | 8/1982 | Terahara et al. | 549/292 |
|---|---|---|---|
| 4,376,863 | 3/1983 | Lam | 549/292 |
| 4,410,629 | 10/1983 | Terahara et al. | 549/292 |
| 4,448,979 | 5/1984 | Terahara et al. | 549/292 |
| 4,517,373 | 5/1985 | Terahara et al. | 549/292 |

FOREIGN PATENT DOCUMENTS

| 0094443 | 2/1983 | European Pat. Off. | 549/292 |
|---|---|---|---|
| 0137445 | 4/1985 | European Pat. Off. | 549/292 |
| 122483A | 7/1984 | Japan | 549/292 |

*Primary Examiner*—Glennon H. Hollrah
*Assistant Examiner*—D. L. Dinner
*Attorney, Agent, or Firm*—Joseph F. DiPrima; William H. Nicholson

[57] ABSTRACT

Novel 3-hydroxy-3-methylglutaryl-coenzyme A (HMG-CoA) reductase inhibitors which are useful as antihypercholesterolemic agents and are represented by the following general structural formulae (I) or (II):

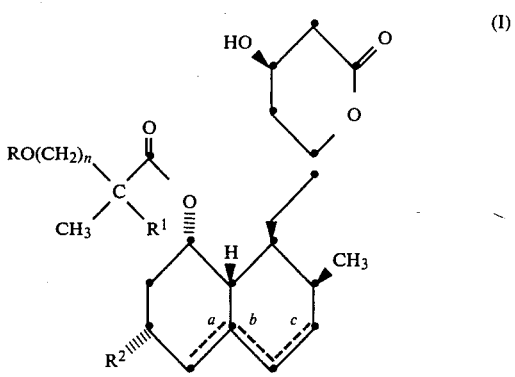

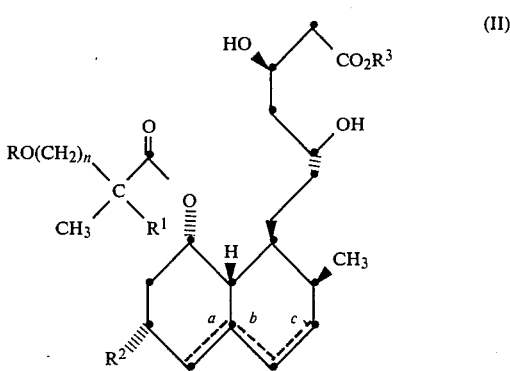

wherein:
n is 1 to 5;
R is hydrogen or

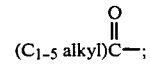

$R^1$ is hydrogen or methyl;
$R^2$ is hydrogen or methyl; and
$R^3$ is hydrogen, $C_{1-5}$ alkyl or $C_{1-5}$ alkyl substituted with a member of the group consisting of phenyl, dimethylamino, or acetylamino; and the dotted lines at a, b and c represent optional double bonds and pharmaceutically acceptable salts of the compounds (II) in which $R^3$ is hydrogen are disclosed.

17 Claims, No Drawings

NOVEL HMG-COA REDUCTASE INHIBITORS

BACKGROUND OF THE INVENTION

Hypercholesterolemia is known to be one of the prime risk factors of cardiovascular disease such as arteriosclerosis, and there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. The naturally occurring compounds and their semi-synthetic analogs have the following general structural formulae:

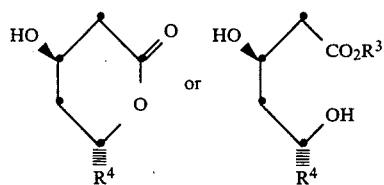

wherein:

$R^3$ is hydrogen, $C_{1-5}$ alkyl or $C_{1-5}$ alkyl substituted with a member of the group consisting of phenyl, dimethylamino, or acetylamino;

$R^4$ is

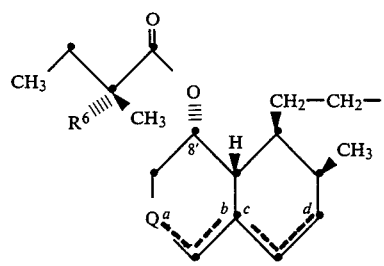

wherein

Q is

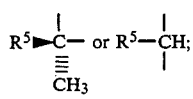

$R^5$ is H or OH:

$R^6$ is hydrogen or methyl; and a, b, c, and d represent optional double bonds, especially where b and d represent double bonds or a, b, c, and d are all single bonds.

U.S. Pat. No. 4,517,373 discloses semi-synthetic hydroxy containing compounds represented by the above general formula wherein $R^4$ is

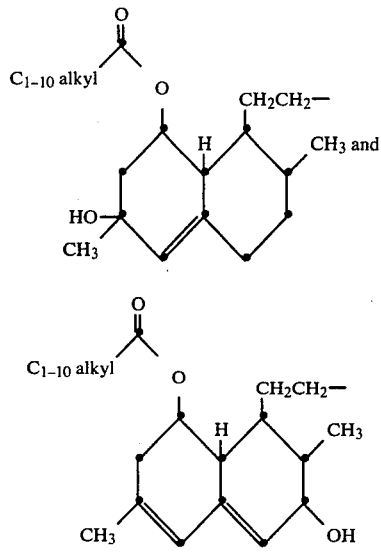

U.S. Pat. No. 4,346,227 and U.S. Pat. No. 4,448,979 also disclose semi-synthetic hydroxy containing compounds represented by the above general formula wherein $R^4$ is

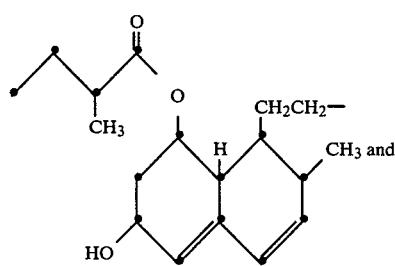

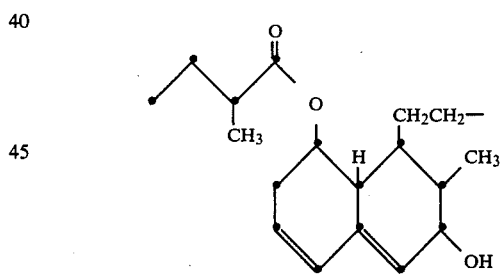

U.S. Pat. No. 4,376,863 discloses a fermentation product isolated after cultivation of a microorganism belonging to the genus Aspergillus which has a hydroxy containing butyryloxy side chain and is represented by the above general formula wherein $R^4$ is

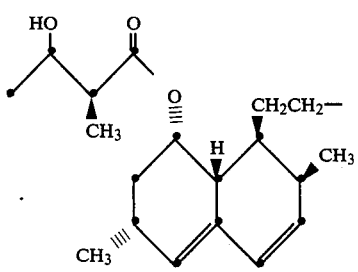

Japanese unexamined patent application No. J59-122,483-A discloses a semi-synthetic hydroxy-containing compound represented by the above general formula wherein $R^4$ is

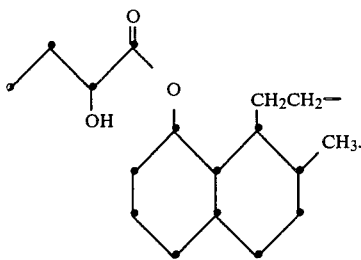

SUMMARY OF THE INVENTION

This invention relates to novel compounds which are HMG-CoA reductase inhibitors and are useful as antihypercholesterolemic agents. Specifically, the compounds of this invention are semi-synthetic analogs of compactin and mevinolin and the dihydro and tetrahydro analogs thereof which possess a terminal hydroxy group or a $C_{2-6}$ alkanoyloxy substituent on the terminal carbon of the 8'-ester acyl moiety. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

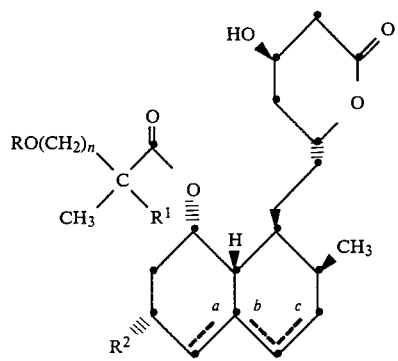

(I)

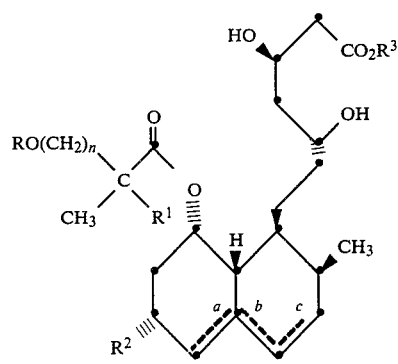

(II)

wherein:

n is 1 to 5;
R is hydrogen or

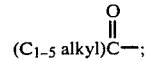

$R^1$ is hydrogen or methyl;
$R^2$ is hydrogen or methyl; and
$R^3$ is hydrogen, $C_{1-5}$ alkyl or $C_{1-5}$ alkyl substituted with a member of the group consisting of phenyl, dimethylamino, or acetylamino; and
the dotted lines at a, b and c represent optional double bonds and pharmaceutically acceptable salts of the compounds (II) in which $R_3$ is hydrogen.

A preferred embodiment of this invention is the class of compounds of the formulae (I) and (II) wherein n is 1 to 3 and $R^2$ is methyl. A sub-class of these compounds is exemplified by the compounds containing one double bond at a, b or c or two double bonds, a and c, in the decahydronaphthalene moiety.

A more preferred embodiment of this invention is the class of compounds of the formulae (I) and (II) wherein n is 1 to 3, $R^2$ is methyl and the dotted lines at a and c are representative of double bonds. Illustrative of this embodiment is 6(R)-[2-[8(S)-(2-methyl-4-hydroxybutyryloxy)-2(S),6(R)-dimethyl-1,2,6,7,8,8a(R)-hexahydronaphthyl-1-(S)]ethyl]-4(R)-hydroxy-3,4,5,6-tetrahydro-2H-pyran-2-one and the corresponding ring opened dihydroxy acids.

The most preferred embodiment of this invention is the class of compounds of the formulae (I) and (II) wherein n is 1 to 3 and $R^1$ and $R^2$ are methyl and the dotted lines at a and c are representative of double bonds. Exemplifying this embodiment are 6(R)-[2-[8(S)-(2,2-dimethyl-4-hydroxybutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2one, 6(R)-[2-[8(S)-(2,2-dimethyl-5-hydroxypentanoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one, and 6(R)-[2-[8(S)-(2,2-dimethyl-3-hydroxypropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one and the corresponding ring opened dihydroxy acids.

Another preferred embodiment of this invention is the class of compounds of the formula (II) wherein $R^3$ is hydrogen or $C_{1-5}$ alkyl and pharmaceutically acceptable salts of the compounds of the formula (II) wherein $R^3$ is hydrogen.

The pharmaceutically acceptable salts of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of formula (I) are conveniently prepared from compactin, mevinolin or the appropriate dihydro or tetrahydro analog thereof via the following general synthetic pathway:

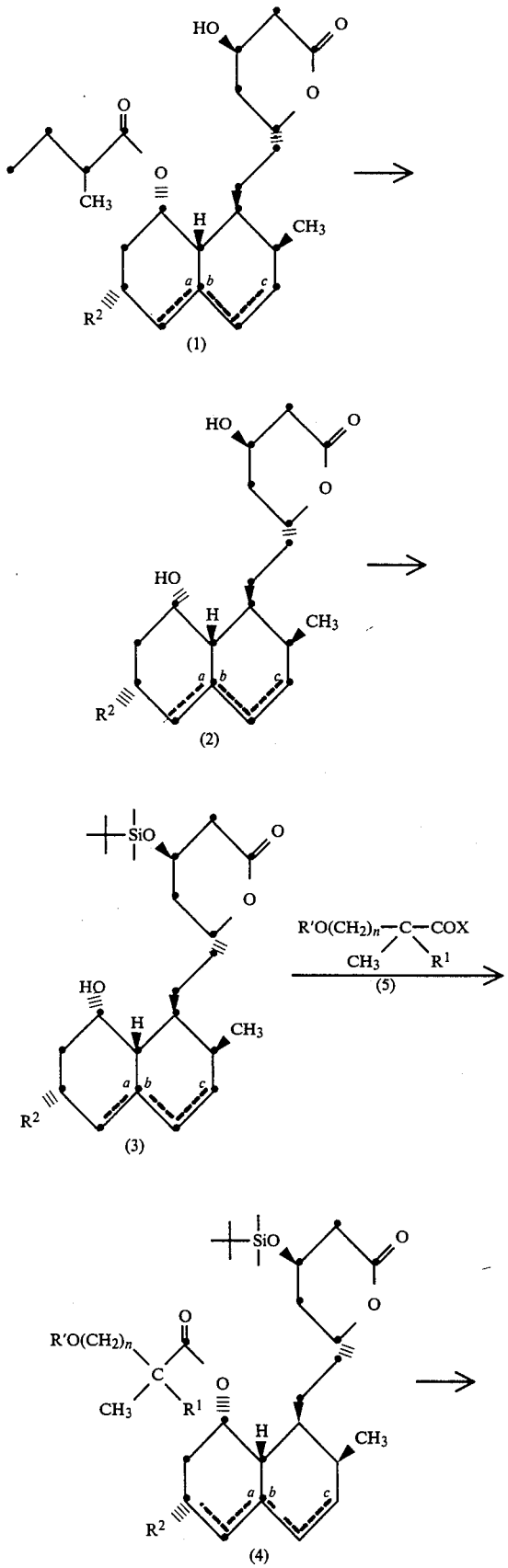

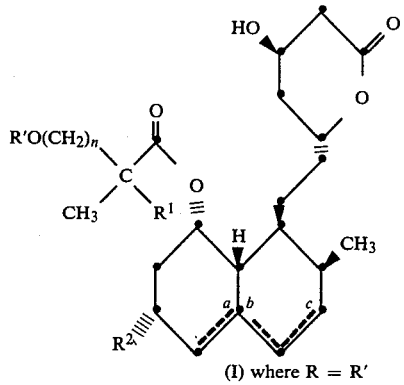

The starting materials compactin, mevinolin and their dihydro and tetrahydro analogs are readily available or may be prepared according to fermentation procedures disclosed in U.S. Pat. No. 3,983,140, U.S. Pat. No. 4,049,495, U.S. Pat. No. 4,231,938, and U.S. Pat. No. 4,294,846 and the hydrogenation procedures disclosed in U.S. Pat. No. 4,351,844. The appropriate starting material of formula (1) is then hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butylsilyl group, according to the procedure disclosed in U.S. Pat. No. 4,444,784. Acylation of the 8' hydroxy group of the compounds of the formula (3) is accomplished under suitable conditions utilizing the appropriately substituted acid halides of the formula (5) wherein n and $R^1$ are as described above, X is chloro or bromo, preferably chloro, and R' is a suitable protecting group such as

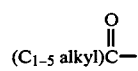

to afford the compounds of the formula (4). The protecting group at the 4-position of the lactone moiety of the compounds of formula (4) is removed utilizing suitable conditions to afford the compounds of the formula (I) wherein R is

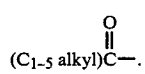

To arrive at the compounds of formula (I) wherein R is hydrogen, the R' group is removed under suitable conditions, such as basic conditions where R' is a

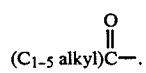

The appropriately substituted acid halides of the formula (5) are conveniently prepared from known starting material utilizing standard chemical transformations.

The synthesis of these compounds of the formula (5) wherein n is 2 or 3 is accomplished as follows:

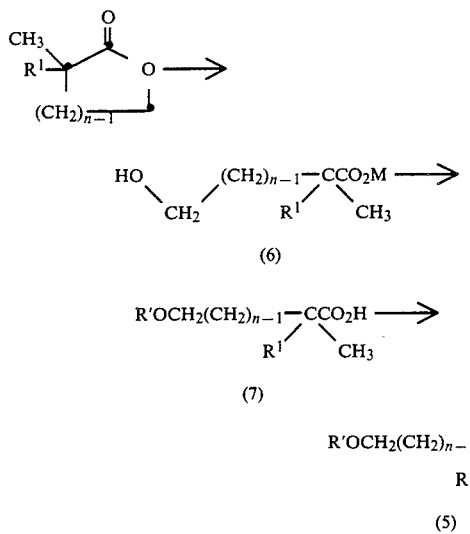

(6)

$$R'OCH_2(CH_2)_{n-1}\underset{R^1}{\overset{}{-}}\underset{CH_3}{\overset{CCO_2H}{-}} \longrightarrow$$

(7)

$$R'OCH_2(CH_2)_{n-1}\underset{R^1}{\overset{}{-}}\underset{CH_3}{\overset{CCOX}{-}}$$

(5)

Specifically, when n is 2 dihydro-3-methyl-2(3H)furanone or dihydro-3,3-dimethyl-2(3H)furanone is treated with an alkali metal hydroxide, such as sodium hydroxide, followed by acylation with a $C_{2-6}$ alkanoyl anhydride, such as acetic anhydride and the resulting carboxylic acid of the formula (7) is then treated with an acid halide-forming agent, such as oxalyl chloride, to yield the desired acid halide of the formula (5). For the compounds of the formula (5) wherein n is 3, the analogous starting materials tetrahydro-3-methyl-2(2H)pyranone or tetrahydro-3,3-dimethyl-2(2H)pyranone are used.

The synthesis of the compounds of formula (5) wherein n is 1 is started from the readily available 3-hydroxypropionic acids of the formula (6).

The compounds of the formula (II) wherein $R^3$ is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein $R^3$ is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:1 and 1:15,000.

The intrinsic HMG-CoA reductase inhibition activity of the claimed compounds is measured in the in vitro protocol described below:

The In Vitro Determination of HMG-CoA Reductase Activity in Liver and the In Vitro Testing of Inhibitors The procedure to measure in vitro HMG-CoA reductase activity in rat liver involves two steps and is based upon the procedure of Alberts et al:[1]

1. Preparation of liver microsomal pellets.
2. Assay of the pellet for HMG-CoA reductase activity.

Preparation of Microsomal Pellet

Microsomes are prepared from livers of 150-200 g male rats (Charles River) maintained for a week on ground chow containing 2.0% cholestyramine, a bile acid sequestrant. The rats are sacrificed by cervical dislocation, and the livers removed immediately and chilled on ice. All subsequent operation are carried out at 0°-5° C.

Preparation of Microsomal Pellet from Rat Livers
Buffer Solutions
  Buffer I (for homogenization)
    50 mM $KPO_4$ pH 7.0
    0.2M sucrose
    2 mM DTT
  Buffer I+EDTA (for washing pellet)
    50 mM $KPO_4$ pH 7.0
    0.2M sucrose
    2 mM DTT
    50 mM EDTA
Procedure: all operation at 4° C.
1. Animals are sacrifice. Rinse livers with ice-cold Buffer I.
2. Blot off excess liquid, weight livers.
3. Add 2 vol. of Buffer I.
4. Mince and homogenize at 1000 rpm, 10 ups and downs.
5. Centrifuge homogenate at 12,000 rpm×15 min. discard pellet.
6. Centrifuge supernatant at 40K rpm×75 min.
7. Pour off supernatant.
8. Wash pellet with Buffer I+EDTA, vortex vigorously.
9. Centrifuge again at 40K rpm×75 min.
10. Aspirate off supernatant.
11. Freeze pellet at −70° C. until further purification.

Purification of HMG-CoA Reductase from Microsomal Pellet
Buffer Solution
  Buffer A+50% glycerol
    0.1M sucrose
    0.05M KCl
    0.04M $KPO_4$ pH 7.4
    0.03M EDTA
    0.01M DTT
    50% glycerol
  Buffer A
    0.1M sucrose
    0.05M KCl
    0.04M $KPO_4$ pH 7.4
    0.03M EDTA
    0.01M DTT
  Porter Buffer
    0.05M $KPO_4$ pH 7.4
    3 mM DTT
    30% glycerol 1M KCl
0.03M EDTA
Buffer B
0.04M KPO₄ pH 7.4
0.03M EDTA
0.01M DTT Procedure: all operations are carried out at room temperature 1. To each microsomal pellet 3 ml of Buffer A+50% glycerol is added.
2. Homogenize at 1000 rpm, 10 ups and downs.
3. Incubate microsomal homogenate at 37° C. for 60 minutes.
4. Add Buffer A to microsomal homogenate to bring down glycerol concentration to 8% or less.
5. Centrifuge homogenate at 40K rpm×60 min.
6. Do 0–35% (NH₄)₂SO₄ precipitation.
7. Centrifuge at 15K rpm×15 min. discard pellet.
8. To the supernatant, do 35–50% (NH₄)₂SO₄ precipitation.
9. Centrifuge at 15K rpm×15 min. aspirate off supernatant.
10. To each pellet, add 1 ml Porter Buffer, mix well.
11. Do heat treatment at 65° C. for 6 minutes.
12. Centrifuge at 40K rpm×30 min. discard pellet.
13. Dilute supernatant 1:3 with Buffer A to dilute out KCl concentration.
14. Do 0–60% (NH₄)₂SO₄ precipitation.
15. Centrifuge at 15K rpm×15 min. discard supernatant.
16. Take up pellet in least volume of Buffer A.
17. Store at −70° C.

Assay of HMG-CoA Reductase Activity

The complete assay system is in a total volume of 0.8 ml in phosphate buffer at pH 7.2 (100 mM) with the cofactors at the following concentrations: MgCl₂ 3 mM; NADP, 3 mM; glucose-6-phosphate, 10 mM; glucose-6-phosphate dehydrogenase (ED 1.1.1.49) 3.0 enzyme units; reduced glutathione, 50 mM; HMG-CoA (Glutaryl-3-¹⁴C) 0.2 mM (0.1 μCi) and enzyme suspension, 0.1 ml.

The frozen pellet (enzyme) is allowed to thaw at room temperature for 5 minutes and carefully mixed with a stirring rod to a slurry with 0.1 ml of phosphate buffer (pH 7.2) and then diluted to 2.0 ml with the buffer. A volume (0.1 ml) of enzyme suspension is added to each incubation tube. Compounds to be tested are diluted to an appropriate concentration and added in a volume to 10μ before adding the enzyme. An "untreated-control" is run along with the compounds.

The complete system is placed in 16×125 mm screw-cap culture tubes and shaken uncapped in a 37° C. water bath for 40 minutes at 160 oscillations per minute. At the end of this period the reaction is stopped by the addition of 0.4 ml of 8N HCl. 3 Mg of unlabeled mevalonolactone in 0.1 ml H₂O is added and the tubes shaken as before for an additional 30 minutes at 37° C. to ensure lactonization of the biosynthetic mevalonate.

Isolation of Product

200 μl of reaction mixture are applied to Bio-Rex 5 column (5 cm in a Pasteur pipette). Elute three times with one ml each of water into a scintillation vial. Add 10 ml of Aquasol-2, shake and count.

Bio-Rex is an ion-exchange resin, obtained from Bio-Rad. It comes dry in the chloride form and only the 100–200 mesh should be used. It is swelled in water for several hours; any fine particles should be decanted off as these will impair the flow rate. The hydrated resin should be stored at 4°.

Calculation of % Inhibition

Each assay includes 2 untreated controls plus a "killed control" (reaction is stopped immediately before incubation by addition of 0.4 ml of 8N HCl).

After subtracting killed control CPM from all samples, percent inhibition by the test compounds is calculated as follows:

$$\% \text{ Inhibition} = \frac{\text{Untreated Control CPM-Test CPM}}{\text{Untreated Control CPM}} \times 100$$

REFERENCE

1. Alberts, et al., Proceedings of the National Academy of Science, Vol. 77, pp. 3957–61 (1980).

Representative of the intrinsic HMG-CoA reductase inhibitory activities of the claimed compounds tabulated below are a number of claimed compounds and the $IC_{50}$ values and relative potencies thereof.

| Compounds of the Formula (II) | | | | | Relative[1] |
|---|---|---|---|---|---|
| n | R | R¹ | R² | R³ | $IC_{50}$ (μM) | Potency |
| 2 | H | CH₃ | CH₃ | H | 0.0156 | 64 |
| 1 | H | CH₃ | CH₃ | H | 0.02 | 80 |
| 3 | H | CH₃ | CH₃ | H | 0.03 | 63 |
| 2 | H | H | CH₃ | H | 0.04 | 30 |

[1]Relative to compactin arbitrarily assigned a value of 100

Included within the scope of this invention is the method of treating arteriosclerosis, familal hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[8(S)-(2,2-Dimethyl-4-hydroxybutyryloxy)-2(S),6(R)-dimethyl-1,2,6,7,8,8a(R)-hexahydronaphthyl-1(S)ethyl]-4(R)-hydroxy-3,4,5,6-tetrahydro-2H-pyran-2-one (a) 6(R)-[2-[8(S)-Hydroxy-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (2)

A mixture of 20.0 g (49.4 mmol) of mevinolin and 20.7 g (0.493 mol) of LiOH·H₂O in 1.5 L of water was stirred at reflux for 72 hours. The reaction mixture was cooled to 0° C., acidified by addition of 50 ml of conc HCl and then extracted with ether (3×500 ml). The combined extracts were washing with water (3×500 ml) and satd. brine (500 ml), dried (MgSO₄) and evaporated to give a white solid. This solid was dissolved in 300 ml of toluene and heated at reflux for 2 hours in a Dean-Stark apparatus for azeotropic removal of water. After evaporation of the toluene, the residual oily solid was heated at reflux in hexane (150 ml) for 30 minutes. After cooling to 0° C., the hexane solution was filtered and the collected solid was dried in air to yield an off-white powder. An analytical sample was prepared by recrystallization of a portion of this material from 1-chlorobutane to give white clusters: m.p. 128°–131° C. (vac).

Anal. Calc'd for $C_{19}H_{28}O_4 \cdot 0.1C_4H_9Cl$: C, 70.67; H, 8.84. Found: C, 70.77; H, 8.75.

(b) 6(R)-[2-[8(S)-Hydroxy-2(S),6(R)-dimethyl-1,2,6,7,8,8a(R)-hexahydronaphthyl-1(S)-ethyl]-4(R)-tert-butyldimethylsilyloxy-3,4,5,6-tetrahydro-2H-pyran-2-one A mixture of 18.3 g (57.1 mmol) of alcohol from Example 1(a), 12.9 g (85.6 mmol) of tert-butyldimethylchlorosilane and 11.6 g (171.2 mmol) of imidazole in 200 ml of DMF was stirred at 20° C. for 18 hours. The reaction mixture was diluted with 1.5 L of ether and washed successively with water, 2% aq HCl, water and satd. aq $NaHCO_3$. The ether solution was dried ($MgSO_4$), filtered and reduced to one liter. After addition of 600 ml of hexane, the volume was reduced to 600 ml on a steam bath. Crystallization at room temperature provided the silyl ether as a white, cottony solid: m.p. 142°–144° C. (vac).

Anal. Calcd for $C_{25}H_{42}O_4Si$: C, 69.08; H, 9.74. Found: C, 69.46; H, 9.83.

(c) Dihydro-3,3-dimethyl-2(3H)furanone[1]

The dihydro-3-methyl-2(3H)furanone (10.0 g, 0.1 mol) was slowly added to a cold (−78° C.), THF solution (150 ml) of LDA (0.11 mol) so that the internal temperature did not exceed −65° C. After stirring for an additional 30 minutes, the acetone/$CO_2$ bath was replaced with a $CH_3CN/CO_2$ bath and $CH_3I$ (21.3 g, 0.15 mol) was added at a rate sufficient to maintain the internal temperature at −30° C. After stirring at −30° C. for another hour the reaction mixture was allowed to warm to 0° C. and quenched by the dropwise addition of 10% HCl (40 ml, 0.116 mol). The resulting mixture was poured into ether (700 ml) and the ether layer was washed with brine (2×50 ml), dried ($MgSO_4$), and evaporated to a yellow oil. The oil was distilled to give desired product as a colorless liquid, $bp_{18}$ 80°–82° C.

[1]Klunt, W. E.; Covey, D. F., Ferrendelli, J. A., Mol. Pharmacol. 22, 438–443, 1982.

(d) 2,2-Dimethyl-4-hydroxybutanoic acid sodium salt

A solution of 1N NaOH (89 ml, 89 mmol) and the lactone from Example 1(c) (10.0 g, 87.6 mmol) in methanol (50 ml) was stirred at ambient temperature for 18 hours. The solution was concentrated to dryness in vacuo (bath temperature 50° C.). The residue was suspended in toluene (2×50 ml) and the toluene evaporated in vacuo to provide sodium salt as a white powder.

(e) 4-Acetyloxy-2,2-dimethylbutanoic acid

A mixture of the sodium salt from Example 1(d) (5.3 g, 34.4 mmol) and 4-pyrrolidinopyridine (1 g, 6.9 mmol) in pyridine (20 ml) was cooled to 0° C. (ice/acetone bath). After the acetic anhydride (7.02 g, 68.8 mmol) was added, the cooling bath was removed and the reaction mixture was stirred at ambient temperature for 18 hours. The reaction mixture was cooled to 0° C., acidified with 6N HCl, saturated with NaCl and extracted with ether (3×50 ml). The combined extracts were washed with saturated brine (3×25 ml), dried ($MgSO_4$), and evaporated to give a pale yellow liquid. A NMR spectrum showed that this liquid was a mixture of the acid and lactone. An ether solution of the mixture was extracted with saturated $NaHCO_3$ solution (4×10 ml). The combined extracts were acidified with 6N HCl, and the resulting mixture extracted with ether (3×50 ml). The combined ether extracts were dried ($MgSO_4$), and evaporated to give a pale yellow oil which was distilled to provide the acid as a colorless liquid: $bp_{0.5}$ 103°–104° C.

(f) 4-Acetyloxy-2,2-dimethylbutyrylchloride

A solution of the acid from Example 1(e) (14.0 g, 80.4 mmol), oxalyl chloride (11.2 g, 88.4 mmol) and DMF (4 drops) in benzene (50 ml) was stirred at ambient temperature for 1 hour. The light red solution was distilled to provide the acid chloride as a colorless liquid: $bp_{0.5}$ 72°–74° C.

(g) 6(R)-[2-[8(S)-(4-Acetyloxy-2,2-dimethylbutyryloxy)-2(S),6(R)-dimethyl-1,2,6,7,8,8a(R)-hexahydronaphthyl-1(S)]ethyl]-4(R)-tert-butyldimethylsilyloxy-3,4,5,6-tetahydro-2H-pyran-2-one A stirred solution of the alcohol from Example 1(b) (8.9 g, 20.5 mmol), 4-pyrrolidinopyridine (610 mg, 4.1 mmol) and the acid chloride from Example 1(f) (3.9 g, 20.5 mmol) in pyridine (50 ml) was heated under a nitrogen atmosphere at 100° C. After 2 hours, 4 hours and 10 hours, another 1.95 g of the acid chloride was added and the reaction solution was stirred for a total of 18 hours. After cooling to 60° C., the pyridine was removed (in vacuo) and the residue was diluted with ether (500 ml). The resulting mixture was washed with 1N HCl (2×25 ml), satd. $NaHCO_3$ solution (25 ml), satd. brine (2×50 ml) and dried ($MgSO_4$). Evaporation of the ether solution gave the crude produce as a yellow liquid. This liquid was chromatographed on a 17.5×7 cm column of silica gel (230–400 mesh). Elution (under air pressure) with acetone-methylene chloride (1:99, v:v) provided the ester contaminated with acid and acid chloride which was used in the next step without further purification.

(h) 6(R)-[2-[8(S)-(4-Acetyloxy-2,2-dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one A solution of the crude ester from Example 1(g) (12.3 g, 20.8 mmol) in THF (100 ml) was treated with acetic acid (4.7 ml, 83.2 mmol) and a 1M solution of tetrabutylammonium fluoride in THF (62.4 ml, 62.4 mmol) and was stirred at ambient temperature for 20 hours. The reaction mixture was diluted with ether (500 ml) washed with 1.5N HCl (50 ml), satd. NaHCO (50 ml) and satd. brine (2×50 ml) and dried ($MgSO_4$). The solvent was evaporated to provide a pale yellow oil which was used in the next step without further purification.

(i) 6(R)-[2-[8(S)-(2,2-Dimethyl-4-hydroxybutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one A solution of the crude lactone from Example 1(h) 10.1 g, 21.8 mmol) and 10N NaOH (5.45 ml, 54.5 mmol) in methanol (100 ml) was stirred at ambient temperature for 2 hours. The solution was evaporated in vacuo and the residue was cooled (ice/water bath) and acidified with 3N HCl and extracted with ether (3×200 ml). The combined extracts were washed with satd. brine (2×25 ml), dried (MgSO$_4$) and evaporated to give a viscous tan oil. The oil was dissolved in toluene (300 ml) and heated at reflux for 3 hours in a Dean-Stark apparatus in order to relactonize the dihydroxy acid. The toluene was removed in vacuo and the crude lactone was chromatographed on a 18×7 cm column of silica gel (230–400 mesh). Elution (under air pressure) with acetone-methylene chloride (7:13; v:v) provided the lactone as a colorless solid. The solid was recrystallized from ether/hexane to provide the title compound. m.p. 124°–126° C.

TLC Data: R$_f$ 0.28 [MK 6F silica gel, acetone-methylene chloride (7:13; v:v)].

Anal. Calc'd for C$_{25}$H$_{38}$O$_6$: C, 69.09; H, 8.81. Found: C, 68.99; H, 8.58.

EXAMPLE 2

Preparation of 6(R)-[2-[8(S)-(2 methyl-4-hydroxybutyryloxy)-2(S),6(R)-dimethyl-1,2,6,7,8,8a(R)-hexahydronaphthyl-1(S)ethyl]-4(R)-hydroxy-3,4,5,6-tetrahydro-2H-pyran-2-one (a) 2-Methyl-4-hydroxybutanoic acid sodium salt Employing the procedure of Example 1(d) but using dihydro-3-methyl-2(3H)furanone (30 g, 0.3 mol) the title compound was obtained as a white solid and was used without further purification in the following step. NMR (D$_2$O) δ1.10 (3H, d, J=7H), 1.37–2.00 (2H, m), 2.18–2.57 (H, m), 3.60 (2H, t, J=7 Hz).

(b) 4-Acetoxy-2-methylbutanoic acid

Employing the procedure of Example 1(e) but using compound from Example 2(a) (38.7 g, 0.276 mol) the title compound was obtained as a pale yellow liquid. b.p.$_{0.1}$ 102°–105° C., NMR (CDCl$_3$) δ1.23 (3H, d, J=7 Hz), 1.60–2.27 (2H, m), 2.02 (3H, s), 2.43–2.50 (H, m), 4.10 (2H, t, J=7 Hz).

(c) 4-Acetoxy-2-methylbutyryl chloride

Employing the procedure of Example 1(f), but using the compound from Example 2(b) (9.2 g, 0.057 mol), the title compound was obtained as a colorless liquid, b.p.$_{0.3}$ 60°–61° C.

NMR (CDCl$_3$) δ1.33 (3H, d, J=7 Hz), 1.63–2.40 (2H, m), 2.03 (3H, s), 2.77–3.20 (H, m), 4.13 (2H, +, J=7 Hz).

(d) 6(R)-[2-[8(S)-(2-methyl-4-hydroxybutyryloxy)-2(S),6(R)-dimethyl-1,2,6,7,8,8a(R)-hexahydronaphthyl-1(S)ethyl]-4(R)-hydroxy-3,4,5,6-tetrahydro-2H-pyran-2-one Employing the general procedures in Example 1(g) through 1(i), the compound from Example 2(c) was converted into the title compound, m.p. 124°–8° C.

Anal. Calcd. for C$_{24}$H$_{36}$O$_6$: C, 68.54; H, 8.63. Found: C, 68.57; H, 8.97.

EXAMPLE 3

Preparation of 6(R)-[2-(8(S)-(2,2-dimethyl-3-hydroxypropionoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) 3-Acetoxy-2,2-dimethylpropionic acid Acetyl chloride (4.52, 58.2 mmol) was added dropwise to a cold (0° C.) pyridine solution (10 ml) of 2,2-dimethyl-3-hydroxypropionic acid (5.5 g, 46.5 mmol) and 4-DMAP (0.57 g, 4.65 mmol). After stirring overnight at ambient temperature, the reaction was poured into ether (200 ml). This mixture was washed with 10% HCl (2×20 ml), and saturated brine (2×25 ml) and the resulting ethereal solution was dried (MgSO$_4$). Evaporation gave the title compound as a pale yellow solid which was used in the next step without further purification. NMR (CDCl$_3$) δ4.13 (2H, s), 2.08 (3H, s), 1.26 (6H, s).

(b) 3-Acetoxy-2,2-dimethylpropionyl chloride

A benzene solution (25 ml) of crude 3-acetoxy-2,2-dimethyl propionic acid from Example 3(a) (7.4 g, 46.5 mmol), oxalyl chloride (6.45 g, 51 ml) and DMF (2 drops) was stirred at ambient temperature for 3 hours. The pale yellow solution was distilled to provide the title compound as a colorless liquid, b.p.$_{15}$ 85°–88° C. NMR (CDCl$_3$) δ4.18 (2H, s), 2.08 (3H, s), 1.35 (6H, s).

(c) 6(R)-[2-(8(S)-(2,2-dimethyl-3-hydroxypropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Employing the general procedures in Example 1(g) through 1(i), the compound from Example 3(b) was converted into the title compound, m.p. 162°–5° C.

Anal. Calcd. for C$_{24}$H$_{36}$O$_6$: C, 68.54; H, 8.63. Found: C, 68.41; H, 8.76.

EXAMPLE 4

Preparation of 6(R)-[2-[8(S)-(2,2-dimethyl-5-hydroxypentanoyloxy)-2(S),6(R)-dimethyl-1,2,6,7,8,8a(R)-hexahydronaphthyl-1(S)ethyl]-4(R)-hydroxy-3,4,5,6-tetrahydro-2H-pyran-2-one (a) 3-Methyltetrahydro-2H-pyran-2-one Tetrahydro-2H-pyran-2-one (10.0 g, 0.10 mol) was slowly added to a cold (−78° C.) THF solution (100 ml) of LDA (0.11 mol) so that the internal temperature did not exceed −65° C. After stirring for an additional 30 minutes, the acetone/CO$_2$ bath was removed and CH$_3$I (21.3 g, 0.15 mol) was added dropwise. When the internal temperature reached −30° C. the reaction was placed in a CH$_3$CN/CO$_2$ bath to maintain the internal temperature at −35±5° C. After stirring for 1 hour, the reaction mixture was allowed to warm to 0° C. and was quenched by the dropwise addition of sat. NH$_4$Cl solution. The resulting mixture was poured into ether (300 ml) and the ether layer was separated and washed with H$_2$O (50 ml), 1N HCl (25 ml), saturated brine (2×50 ml), dried (MgSO$_4$) and evaporated to provide an orange oil. Distillation of the oil gave the title compound as colorless oil. b.p.$_{15}$ 103°–105° C. NMR (CDCl$_3$) δ4.32 (2H, m), 2.58 (H, m), 2.08 (H, m), 1.84 (2H, m), 1.52 (H, m), 1.26 (3H, d, J=7 Hz).

(b) 3,3-Dimethyltetrahydro-2H-pyran-2-one

The 3-methyltetrahydro-2H-pyran-2-one from Example 4(a) (5.6 g, 49.0 mmol) was slowly added to a cold (−78° C.) THF solution (50 ml) of LDA (54 mmol) so that the internal temperature did not exceed −65° C. After stirring for an additional 30 minutes, the acetone/CO$_2$ bath was replaced with a CH$_3$CN/CO$_2$ bath and CH$_3$I (10.4 g, 73.5 mmol) was added at a rate sufficient to maintain the internal temperature at −45° C. After stirring at −45° C. for an additional hour the reaction was allowed to warm to −30° C. and quenched by the dropwise addition of 10% HCl (21 ml). The resulting mixture was poured into ether (300 ml) and the ether layer was washed with saturated brine (50 ml), saturated NaHCO$_3$ solution (20 ml), saturated brine (2×25 ml), dried (MgSO$_4$) and evaporated to provide a pale yellow oil. This oil was distilled to give the title compound as a colorless liquid. b.p.$_{0.2}$ 54° C. NMR (CDCl$_3$) δ4.34 (2H, m), 1.89 (2H, m), 1.75 (2H, m), 1.30 (6H, s).

(c) 2,2-Dimethyl-5-hydroxypentanoic acid sodium salt

Employing the procedure of Example 1(d), but using the compound from Example 4(b) (5.0 g, 39 mmol), the title compound was obtained as a white solid and was used without further purification in the following step. NMR (D$_2$O) δ3.57 (2H, m), 1.47 (4H, m), 1.10 (6H, s).

(d) 5-Acetyloxy-2,2-dimethylpentanoic acid

Employing the procedure of Example 1(e), but using the compound from Example 4(c) (6.5 g, 38.6 mmol), the title compound was obtained as a colorless liquid. b.p.$_{0.2}$ 120°-124° C. NMR (CDCl$_3$) δ4.06 (2H, m), 2.06 (3H, s), 1.62 (4H, m), 1.22 (6H, s).

(e) 5-Acetyloxy-2,2-dimethylpentanoyl chloride

Employing the procedure of Example 1(f), but using the compound from Example 4(d) (2.4 g, 12.7 mmol), the title compound was obtained as a colorless liquid. b.p.$_{0.2}$ 72°-74° C. NMR (CDCl$_3$) δ4.06 (2H, m), 2.06 (3H, s), 1.68 (4H, m), 1.31 (6H, s).

(f) 6(R)-[2-[8(S)-(2,2-dimethyl-5-hydroxypentanoyloxy)-2(S),6(R)-dimethyl-1,2,6,7,8,8a(R)-hexahydronaphthyl-1-(S)]ethyl]-4(R)-hydroxy-3,4,5,6-tetrahydro-2H-pyran-2-one Employing the general procedures in Example 1(g) through 1(i), the compound from Example 4(e) was converted into the title compound. m.p. 90°-93° C.

Anal. Calcd. for C$_{26}$H$_{40}$O$_6$·0.1CH$_2$Cl$_2$: C, 68.58; H, 8.87. Found: C, 68.63; H, 9.00.

EXAMPLES 5 TO 15

Utilizing the general procedures of Examples 1 to 4 the following compounds of the formula (I) in the following table are prepared from the appropriate acid chloride and compactin, mevinolin, and the dihydro and tetrahydro analogs thereof.

| Compound | n | R | R$^1$ | R$^2$ | a | b | c |
|---|---|---|---|---|---|---|---|
| 5 | 5 | H | CH$_3$ | CH$_3$ | db | — | db |
| 6 | 2 | H | CH$_3$ | CH$_3$ | db | — | db |
| 7 | 3 | H | CH$_3$ | CH$_3$ | — | db | — |
| 8 | 2 | H | CH$_3$ | CH$_3$ | db | — | — |
| 9 | 1 | H | CH$_3$ | CH$_3$ | — | — | db |
| 10 | 2 | H | CH$_3$ | CH$_3$ | — | — | — |
| 11 | 2 | CH$_3$CO | CH$_3$ | H | db | — | db |
| 12 | 1 | C$_3$H$_7$CO | H | H | — | — | — |
| 13 | 5 | H | CH$_3$ | H | — | db | — |
| 14 | 1 | H | H | H | db | — | db |
| 15 | 3 | H | CH$_3$ | H | db | — | db | db = double bond

EXAMPLE 16

Preparation of 7-[1,2,6,7,8,8a(R)-Hexahydro-2(S),6(R)-dimethyl-8(S)-(2,2-dimethyl-4-hydroxybutyryloxy)naphthyl-1(S)]-3(R),5(R)-dihydroxyheptanoic acid, ammonium salt The lactone from Example 1(i) (434 mg, 1 mmol) was dissolved with stirring in 0.1N NaOH (1.1 mmol) at r.t. The resulting solution was cooled to 0° C. and acidified by the dropwise addition of 1N HCl. The resulting mixture was extracted with ether (2×50 ml) and the ether extracts were combined, washed with brine (3×25 ml) and dried (MgSO$_4$). The MgSO$_4$ was removed by filtration and the filtrate saturated with ammonia (gas) to give a gum which solidified to provide the ammonium salt; m.p. eff. 160°-162° C. The solid (100 mg) can be recrystallized by dissolution in warm CH$_3$CN/conc. NH$_4$OH (4:1; v:v, 4 ml) followed by dilution with CH$_3$CN to give colorless needles; m.p. eff. 160°-162° C.

TLC Data: R$_f$ 0.22 [MK 6F silica gel, acetic acid-methylene chloride (3:7; v:v].

Anal. Calc'd for C$_{25}$H$_{43}$NO$_7$: C, 63.92; H, 9.23; N, 2.98. Found: C, 63.77; H, 9.40; N, 3.26.

EXAMPLE 17

Preparation of Alkali and Alkaline Earth Salts of Compound II

To a solution of 42 mg of the lactone from Example 1(i) in 2 ml of ethanol is added 1 ml of aqueous NaOH (10$^{-4}$ moles; 1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 18

Preparation of Ethylenediamine Salt of Compound II

To a solution of 0.50 g of the ammonium salt of Compound II from Example 16 in 10 ml of methanol is added 75 μl of ethylenediamine. The methanol is stripped off under vacuum to obtain the ethylenediamine salt of Compound II.

EXAMPLE 19

Preparation of Tris(hydroxymethyl)aminomethane Salt of Compound

To a solution of 202 mg of the ammonium salt of Compound II from Example 16 in 5 ml of methanol is added a solution of 60.5 mg of tris(hydroxymethyl)aminomethane in 5 ml of methanol. The solvent is removed in vacuo to afford the desired tris(hydroxymethyl)aminomethane salt of Compound II.

EXAMPLE 20

Preparation of L-Lysine Salt of Compound II

A solution of 0.001 mole of L-lysine and 0.0011 mole of the ammonium salt of Compound II from Example 16 in 15 ml of 85% ethanol is concentrated to dryness in vacuo to give the L-lysine salt of Compound II.

Similarly prepared are the L-arginine, L-ornithine, and N-methylglucamine salts of Compound II.

EXAMPLE 21

Preparation of Tetramethylammonium Salt of Compound II

A mixture of 68 mg of Compound II from Example 16 in 2 ml of methylene chloride and 0.08 ml of 24% tetramethylammonium hydroxide in methanol is diluted with ether to yield the tetramethylammonium salt of Compound II.

EXAMPLE 22

Preparation of Methyl Ester of Compound II

To a solution of 400 mg of the lactone from Example 1(i) in 100 ml of absolute methanol is added 10 ml 0.1M sodium methoxide in absolute mehanol. This solution is allowed to stand at room temperature for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amylalcohol, isoamylalcohol, 2-dimethylaminoethanol, benzylalcohol, phenethanol, 2-acetamidoethanol, and the like, the corresponding esters are obtained.

EXAMPLE 23

Preparation of free Hydroxy Acids

The sodium salt of the compound II from Example 17 is redissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 24

As a specific embodiment of a composition of this invention, 20 mg of the lactone from Example 1(i) is formulated with sufficient finely divided lactose to provide a total amount of 580 to 590 mg to fill a size 0 hard gelatin capsule.

What is claimed is:

1. A compound represented by the following general structural formula (I):

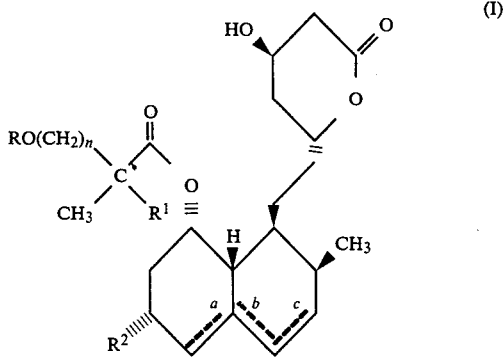

wherein:
n is 1 to 5;
R is hydrogen
$R^1$ is methyl;
$R^2$ is hydrogen or methyl; and the dotted lines at a, b and c represent optional double bonds.

2. A compound of claim 1 wherein n is 1 to 3 and $R^2$ is methyl.

3. A compound of claim 2 wherein one of the dotted lines at a, b or c represents a double bond or the dotted lines at a anc c represent double bonds.

4. A compound of claim 3 wherein the dotted line at a and c represent double bonds.

5. A compound of claim 4 which is 6(R)-[2-[8(S)-(2,2-dimethyl-4-hydroxybutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

6. A compound of claim 4 which is 6(R)-[2-[8(S)-(2,2-dimethyl-5-hydroxypentanoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

7. A compound of claim 4 which is 6(R)-[2-[8(S)-(2,2-dimethyl-3-hydroxypropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

8. A hypocholesterolemic, hypolipidemic pharmaceutical composition comprising a nontoxic therapeutically effective amount of a compound of claim 1 and a pharmaceutically acceptable carrier.

9. A method of inhibiting cholesterol biosynthesis comprising the administration to a warm blooded mammals in need of such treatment a nontoxic therapeutically effective amount of a compound of claim 1.

10. A pharmaceutical composition of claim 8 wherein n is 1 to 3 and $R^2$ is methyl.

11. A pharmaceutical composition of claim 10 wherein one of the dotted lines at a, b or c represents a double bond or the dotted lines at a and c represent double bonds.

12. A pharmaceutical composition of claim 11 wherein to dotted lines at a and c represent double bonds.

13. A pharmaceutical composition of claim 12 wherein the therapeutically active ingredient is selected from
(a) 6(R)-[2-[8(S)-(2,2-dimethyl-4-hydroxybutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;
(b) 6(R)-[2-[8(S)-(2,2-dimethyl-5-hydroxypentanoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and
(c) 6(R)-[2-[8(S)-(2,2-dimethyl-3-hydroxypropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

14. A method of claim 9 wherein n is 1 to 3 and $R^2$ is methyl.

15. A method of claim 10 wherein one of the dotted lines at a, b or c represents a double bond or the dotted lines at a and c represent double bonds.

16. A method of claim 15 wherein the dotted lines at a and c represent double bonds.

17. A method of claim 16 wherein the therapeutically active ingredient is selected from
(a) 6(R)-[2-[8(S)-(2,2-dimethyl-4-hydroxybutyryloxy)-2(S),6(R)-dimethyl-1,2,6,7,8,8a(R)-hexahydronapthyl-1(S)]ethyl]-4(R)-hydroxy-3,4,5,6-tetrahydro-2H-pyran-2-one;

(b) 6(R)-[2-[8(S)-(2,2-dimethyl-5-hydroxypentanoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and (c) 6(R)-[2-[8(S)-(2,2-dimethyl-3-hydroxypropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

* * * * *